United States Patent
Thodeti

(10) Patent No.: US 11,058,707 B2
(45) Date of Patent: Jul. 13, 2021

(54) METHODS FOR TREATING ISCHEMIC HEART DISEASE BY TARGETING TRPV4

(71) Applicant: Northeast Ohio Medical University, Rootstown, OH (US)

(72) Inventor: Charles K. Thodeti, Rootstown, OH (US)

(73) Assignee: Northeast Ohio Medical University, Rootstown, OH (US)

( * ) Notice: Subject to any disclaimer, the term of this patent is extended or adjusted under 35 U.S.C. 154(b) by 0 days.

(21) Appl. No.: 16/178,712

(22) Filed: Nov. 2, 2018

(65) Prior Publication Data

US 2020/0000837 A1 Jan. 2, 2020

Related U.S. Application Data

(60) Provisional application No. 62/691,032, filed on Jun. 28, 2018.

(51) Int. Cl.
| | |
|---|---|
| *A61K 31/7105* | (2006.01) |
| *A61K 31/425* | (2006.01) |
| *A61K 31/381* | (2006.01) |
| *A61P 9/04* | (2006.01) |
| *A61P 9/10* | (2006.01) |
| *A61K 31/4439* | (2006.01) |

(52) U.S. Cl.
CPC ........ *A61K 31/7105* (2013.01); *A61K 31/381* (2013.01); *A61K 31/425* (2013.01); *A61K 31/4439* (2013.01); *A61P 9/04* (2018.01); *A61P 9/10* (2018.01)

(58) Field of Classification Search
CPC ..... C07C 45/673; C07C 49/84; C07C 49/255; A61K 31/00; A61K 38/00; A61K 45/06
USPC .................... 435/6.1, 91.1, 91.31, 455, 458; 514/44 A; 530/300, 350; 536/23.1, 24.5
See application file for complete search history.

(56) References Cited

U.S. PATENT DOCUMENTS

| 8,394,779 | B2 | 3/2013 | Ingber et al. | |
|---|---|---|---|---|
| 2019/0002527 | A1* | 1/2019 | Ingber | C07K 14/70596 |

OTHER PUBLICATIONS

Rahaman et al, J. Clin. Invest., vol. 124, No. 12, pp. 5225-5238. (Year: 2015).*
Adapala et al, Poster No. 24061, 2017 American Heart Association Late Breaking Basic Science Abstracts, Circulation Res., e-93-94. (Year: 2017).*
Turner et al, Clinical & Experimental Cardiology, vol. 6, No. 3, p. 1000355, pp. 1-5. (Year: 2015).*
Thorneloe et al, Science Translational Medicine, vol. 4, No. 159, 159ra148, pp. 1-11. (Year: 2012).*
Zhan et al, Gene, vol. 642, pp. 1-8 (Year: 2017).*
Vincent et al, Biochem. & Biophys. Res. Comm., vol. 389, pp. 490-494 (Year: 2009).*
Adapala et al., "TRPV4 channels mediate cardiac fibroblast differentiation by integrating mechanical and soluble signals", Journal of Molecular and Cellular Cardiology, (2013), vol. 54, pp. 45-52.
Adapala et al., "TRPV4 Channel Deletion Improves Cardiac Function and Remodeling Following Myocardial Infarction and Transverse Aortic Construction via Modulation of Rho/MRTF-A Pathway", Late-Breaking Basic Science Abstracts From the American Heart Association's Scientific Sessions 2014, p. e88.
Adapala et al., "Targeting Trpv4 Channels Protects Heart From Pathological Remodeling Following Myocardial Infarction", Late-Breaking Basic Science Abstracts From the American Heart Association's Scientific Sessions 2017, pp. e95-e96.
Rahaman et al., "TRPV4 mediates myofibroblast differentiation and pulmonary fibrosis in mice", The Journal of Clinical Investigation, (2014), vol. 124, No. 12, pp. 5225-5238.
Turner et al., "Preservation of Cardiac Function and Attenuation of Remodelling in Transient Receptor Potential Vanilloid 4 Knockout Mice Following Myocardial Infarction", Clinical & Experimental Cardiology, (2015), vol. 6, issue 3, pp. 1-5.
Vergnolle, "TRPV4: New therapeutic target for inflammatory bowel diseases", Biochemical Pharmacology, (2014), vol. 89, issue 2, pp. 157-161.
Ye et al., "TRPV4 is a regulator of adipose oxidative metabolism, inflammation and energy homeostasis", NIH-PA Author Manuscript, (2012), vol. 151(1), pp. 96-110.

* cited by examiner

*Primary Examiner* — Jane J Zara

(74) *Attorney, Agent, or Firm* — MacMillan, Sobanski & Todd, LLC

(57) ABSTRACT

Methods useful for treating ischemic heart disease, reducing cardiac fibrosis, improving cardiac function, or increasing coronary angiogenesis are described.

9 Claims, 20 Drawing Sheets

CON

TGFβ1

AB1 + TGFβ1

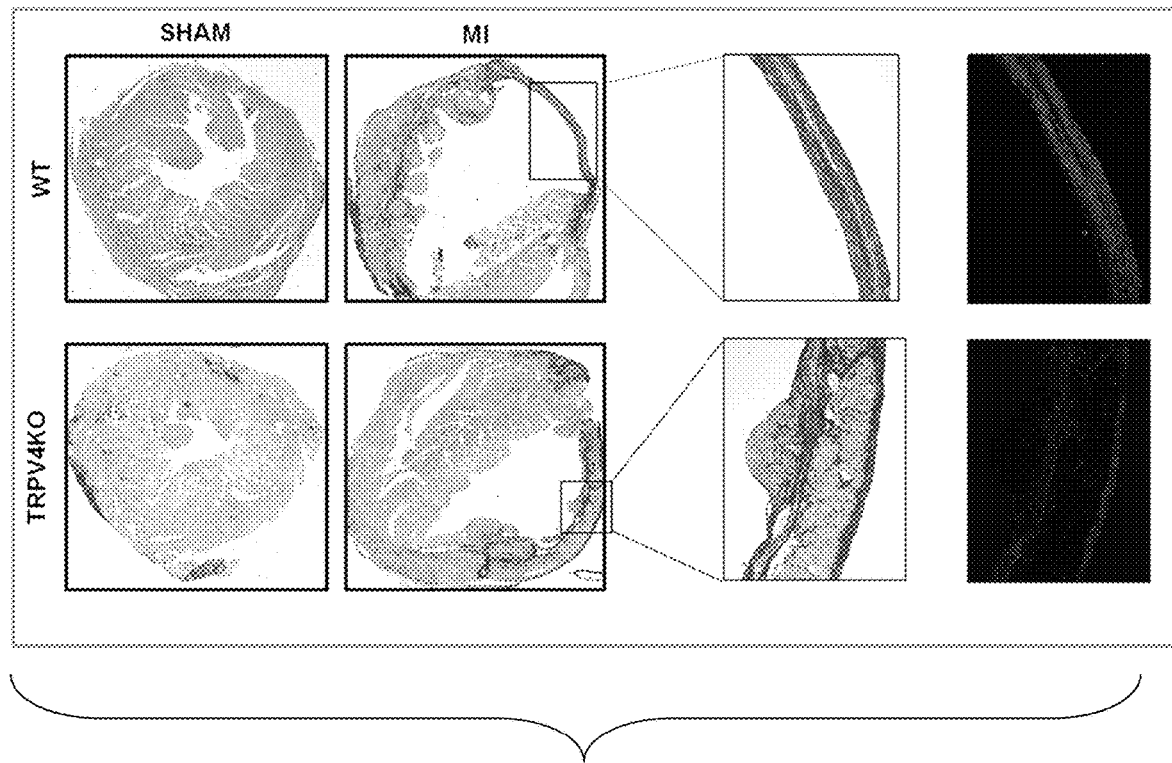
FIG. 10
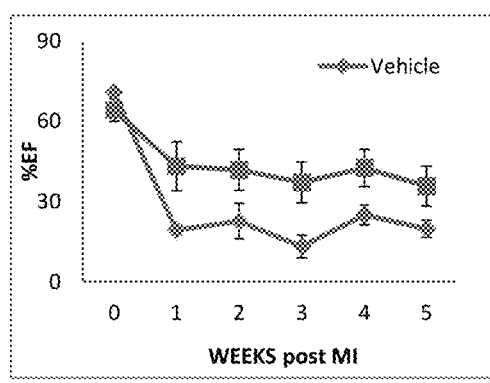
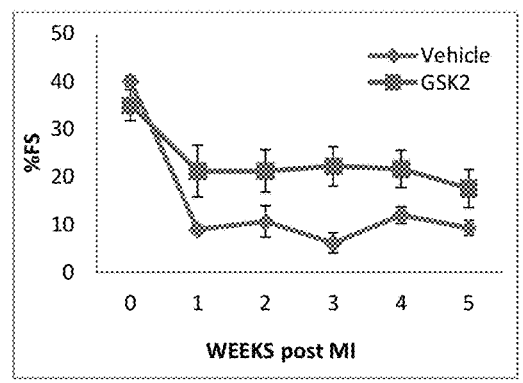
FIG. 11A  FIG. 11B

METHODS FOR TREATING ISCHEMIC HEART DISEASE BY TARGETING TRPV4

RELATED APPLICATIONS

This application claims priority to U.S. Provisional Application Ser. No. 62/691,032 filed under 35 U.S.C. § 111(b) on Jun. 28, 2018, the disclosure of which is incorporated herein by reference in its entirety.

STATEMENT REGARDING FEDERALLY SPONSORED RESEARCH

This invention was made with government support under Grant No. R01HL119705 awarded by NIH-NHLBI. The government has certain rights in the invention.

BACKGROUND OF THE INVENTION

Ischemic heart disease (IHD), also known as coronary artery disease, is the major underlying cause of myocardial infarction, scarring, and hypertrophy leading to heart failure. Each year, almost 300,000 individuals experience recurrent coronary attack, with ischemic heart disease projected to affect 40.5% of the US population in 15 years. This alarming incidence of IHD will add overwhelming individual and social burden that requires advanced treatment modalities and additional research in this area.

Among those suffering from IHD in the United States, myocardial infarction (MI) is one of the major causes of the death. The prevention of ischemic damage due to MI involves scar formation by synthesis and reorganization of extracellular matrix (ECM). Specifically, it involves the differentiation of cardiac fibroblasts (CFs) into highly contractile and hypersecretory myofibroblasts (myoFibs), which secrete ECM components to form a scar. The post-MI adaptation of the heart is important for its long term function in the surviving patients. Therefore, the clinical management of cardiac fibrosis post-MI presents a major challenge in surviving patients. CFs are the primary mediators of cardiac repair as they secrete and remodel extracellular matrix in the heart. CF differentiation to myofibroblasts (myoFibs) is the critical event in acute stages of scar formation, as myoFibs play a major role in wound healing and remodeling of damaged tissue. Importantly, extended activation of myoFibs can cause a net increase in ECM deposition, cardiac fibrosis, and eventual impairment of cardiac performance, which is thought to be related to their hypersecretory functions. Although CF differentiation to myoFibs is believed to be critical in physiological or pathological post-MI remodeling, the molecular mechanism(s) underlying their differentiation is not known.

Most of the past work on CF differentiation to myoFibs focused on soluble mediators such as TGF-β1, Angiotensin II (Ang II), endothelin-1 (ET-1), and platelet derived growth factor (PDGF). Mechanical signals such as stretch and stiff ECM is often concurrent with the development of fibrosis. However, little is known about the molecular mechanism of the integration of TGF-β (chemical) and integrin (mechanical) signaling required for CF differentiation to myoFibs. While many studies have investigated the signaling downstream of TGF-β1 to the α-SMA expression, very little work has been done to investigate signaling molecules that can act as a mechanosensor or integrator of chemical and mechanical signaling in cardiac fibrosis.

Transient receptor potential vanilloid type 4 (TRPV4) is a protein encoded by the TRPV4 gene. The TRPV4 protein is a mechanosensitive, $Ca^{2+}$-permeable, nonselective cation channel that has been shown to be contribute to the pathophysiology of skeletal and neuromuscular diseases. However, its contribution to fibrosis and IHD is largely unknown.

SUMMARY OF THE INVENTION

Provided herein is a method for treating ischemic heart disease, reducing cardiac fibrosis, increasing coronary angiogenesis, and/or improving cardiac function in a subject. In certain embodiments, the method is useful for treating myocardial infarction, scarring, and/or hypertrophy leading to heart failure.

The method includes administering an effective amount of a TRPV4 inhibitor to a subject in need thereof, to inhibit TRPV4 and treat ischemic heart disease in the subject.

In certain embodiments, the TRPV4 inhibitor comprises one or more of siRNAs targeting TRPV4; selective antagonists and nonselective antagonists.

In certain embodiments, the TRPV4 inhibitor is GSK2193874, also known as (3-([1,4'-Bipiperidin]-1'-ylmethyl)-7-bromo-N-(1-phenylcyclopropyl)-2-[3-(trifluoromethyl)phenyl]-4-quinolinecarboxamide.

In certain embodiments, the TRPV4 inhibitor is formulated in a composition with one or more pharmaceutically acceptable excipients, diluents, or carriers. In certain embodiments, the TRPV4 inhibitor is administered at a concentration ranging from about 0.01 μM to about 100 μM. In certain embodiments, the TRPV4 inhibitor is administered at a concentration of about 10 μM. In certain embodiments, the TRPV4 inhibitor is administered to the subject following a myocardial infarction. In certain embodiments, the TRPV4 inhibitor is co-administered with an ischemic heart disease treatment selected from the group consisting of: organic nitrates, beta blockers, calcium channel blockers, statins, antiplatelets, ACE inhibitors, and combinations thereof.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 5A shows the control; FIG. 5B shows TGFβ1; and, FIG. 5C shows AB1+TGFβ1.

FIG. 10 shows histological analysis of heart sections showing increased cardiac fibrosis (Picrosirius-red staining) at the infarct zone as well as in remote zone of WT-MI hearts which is significantly reduced in TRPV4KO-MI hearts.

FIG. 11A shows % EF (ejection fraction=EF) for MI mice given orally a specific TRPV4 antagonist, GSK2193874 (GSK2) (10 mg/Kg/day) or vehicle (0.01% DMSO/water).

FIG. 11B shows % FS (fractional shortening=FS) for MI mice given orally a specific TRPV4 antagonist, GSK2193874 (GSK2) (10 mg/Kg/day) or vehicle (0.01% DMSO/water).

DETAILED DESCRIPTION OF THE INVENTION

Figure 1:
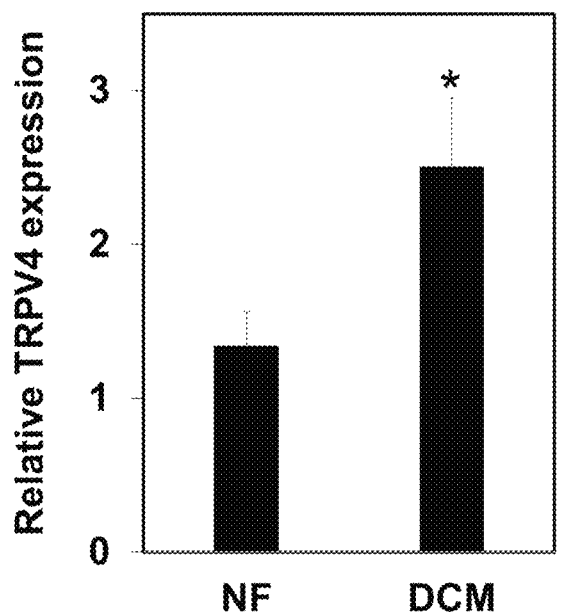
FIG. 1 shows the relative TRPV4 expression; RT-PCR analysis showing increased expression of TRPV4 mRNA in human heart tissues obtained from subjects with dilated cardiomyopathy (DCM) compared to normal subjects (NF=non-failing hearts).

Throughout this disclosure, various publications, patents and published patent specifications are referenced by an identifying citation. The disclosures of these publications, patents, and published patent specifications are hereby incorporated by reference into the present disclosure in their entirety to more fully describe the state of the art to which this invention pertains.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term unless the context clearly indicates otherwise.

As used herein, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

As used herein, the terms "optional" or "optionally" may be taken to mean that the subsequently described structure, event or circumstance may or may not occur, and that the description includes instances where the event occurs and instances where it does not.

As used herein, the term "administering" when used in conjunction with a therapeutic means to administer a therapeutic directly into or onto a target or to administer a therapeutic to a subject whereby the therapeutic positively impacts the area to which it is targeted.

As used herein, the terms "treat," "treating" or treatment" generally mean the exposure of a living organism to one or more physical, chemical or psychological entities or stimuli that may prevent, improve or ameliorate a diseased state. As used herein, the term "treating" refers to both therapeutic treatment and prophylactic or preventative measures.

As used herein, the term "indication" generally refers to a medical condition or symptoms associated with a medical condition.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly.

As used herein, "preventing" means preventing in whole or in part, or ameliorating or controlling.

As used herein, a "therapeutically effective amount" in reference to the compounds or compositions refers to the amount sufficient to induce a sign or any other desired alteration that results in the promotion and/or improvement of a subject's health.

As use herein, the term "improves" generally means changes either the appearance, form, characteristics and/or the physical health.

General Description

It is now shown herein that inhibiting TRPV4 decreases cardiac fibrosis, increases coronary angiogenesis, and improves cardiac function and remodeling following a pressure-overload.

Effective inhibition of TRPV4 can be accomplished with any suitable TRPV4 inhibitor. Suitable TRPV4 inhibitors include, but are not limited to: siRNAs targeting TRPV4; nonselective antagonists such as one or more of:
ammoniated ruthenium oxychloride (also known as ruthenium red);
selective antagonists such as 2,4-dichloro-N-isopropyl-N-(2-isopropylaminoethyl)benzenesulfonamide (also known as AB159908 or RN1734),
2-methyl-1-[3-(4-morpholinyl)propyl]-5-phenyl-N-[3-(trifluoromethyl)phenyl]-1H-pyrrole-3-carboxamide (also known as HC-067047),
N-[2-(4-chlorophenyl)ethyl]-1,3,4,5-tetrahydro-7,8-dihydroxy-2H-2-benzazepine-2-carbothioamide (also known as capsazepine),
3,7-dimethyl-2,6-octadienal (also known as citral), N-(4-(2-(benzyl(methyl)amino)ethyl)phenyl)-5-(pyridin-3-yl)thiazol-2-amine (also known as GSK205), and
3-([1,4'-bipiperidin]-1'-ylmethyl)-7-bromo-N-(1-phenylcyclopropyl)-2-[3-(trifluoromethyl)phenyl]-4-quinolinecarboxamide (also known as GSK2193874).

Suitable TRPV4 inhibitors also include any of the TRPV4 antagonists described in U.S. Pat. No. 8,450,484, WO 2009/111680, WO 2009/146177, WO 2009/146182, WO 2010/011912, WO 2010/011914, and WO 2011/119701 (each of which is hereby incorporated by reference in its entirety). In certain non-limiting examples, the TRPV4 inhibitor is the selective antagonist AB159908.

For example, effective inhibition of TRPV4 is accomplished with the TRPV4 inhibitor 3-([1,4'-bipiperidin]-1'-ylmethyl)-7-bromo-N-(1-phenylcyclopropyl)-2-[3-(trifluoromethyl)phenyl]-4-quinolinecarboxamide (also known as GSK2193874).

In particular embodiments, the TRPV4 inhibitors and compositions described herein are useful for treating various conditions such as, but not limited to, ischemic heart disease. Furthermore, the compounds and compositions herein can be used in combination therapies. That is, the TRPV4 inhibitors and compositions containing the same can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the TRPV4 inhibitor or composition containing the same can be administered in combination with one or more suitable treatments for ischemic heart disease including, but not limited to: organic nitrates, such as isosorbide dinitrate or isosorbide mononitate; beta blockers, such as acebutolol, propanolol, atanolol, labetalol, carvedilol, penbutolol, pindolol, metoprolol, or timolol; calcium channel blockers, such as amlodipine or nifedipine; statins, such as atorvastin or rusvastatin; antiplatelets, such as aspirin, ticagrelor, prasugrel, or clopidogrel; or angiotensin-converting enzyme (ACE) inhibitors, such as benazepril, fosinopril, captopril, enalapril, perindopril, lisinopril, ramipril, trandolapril, or quinapril.

Another non-limiting example of a combination therapy for ischemic heart disease is the combination of a TRPV4 inhibitor or composition containing the same with one or more surgical treatments or lifestyle changes. Suitable surgical treatments include, but are not limited to, angioplasty or coronary artery bypass grafting. Suitable lifestyle changes include, but are not limited to, increasing exercise, weight management, smoking cessation, or dietary changes.

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Example 1—TRPV4 Expression is Increased in the Hearts of Dilated Cardiomyopathy (DCM) Patients FIG. 1 shows the relative TRPV4 expression; RT-PCR analysis showing increased expression of TRPV4 mRNA in human heart tissues obtained from subjects with dilated cardiomyopathy (DCM) compared to normal subjects (NF=non-failing hearts).

Example 6—TRPV4 KO Mice Show, Improved Survival Rate and Cardiac Function in Response to Pressure-Overload-Induced Cardiac Hypertrophy Due to Reduced Cardiac Fibrosis and Increased Coronary Angiogenesis In Vivo Absence of TRPV4 channels preserves cardiac function in response to TAC (transverse aortic constriction) via reducing cardiac fibrosis and increasing coronary angiogenesis.

Figure 2:
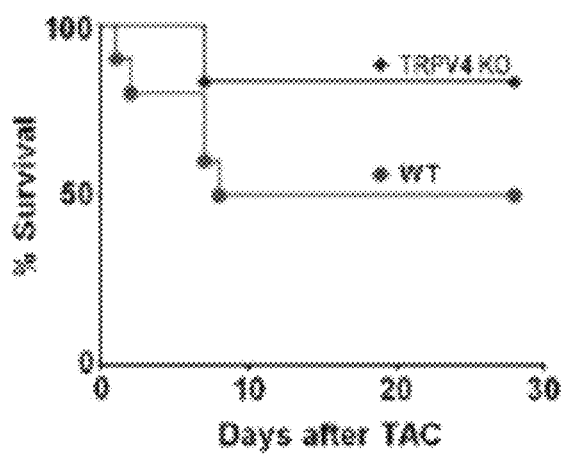
FIG. 2 shows time-dependent survival rates of WT and TRPV4 KO mice subjected to TAC.

A pressure-overload-induced hypertrophy model was used to further confirm the TRPV4 role in cardiac fibrosis in vivo. Pressure-overload was induced in the hearts of TRPV4 KO and wild type mice (C57BL6) by transverse aortic constriction (TAC). The results showed TRPV4 KO mice had improved survival rates compared to the WT mice in response to TAC (FIG. 2).

Deletion of TRPV4 protects heart from pressure-overload-induced hypertrophy (heart failure) in mice. WT and TRPV4KO mice were subjected to pressure-overload with TAC (transverse aortic constriction) surgeries and followed for 28 days.

Figure 3A:
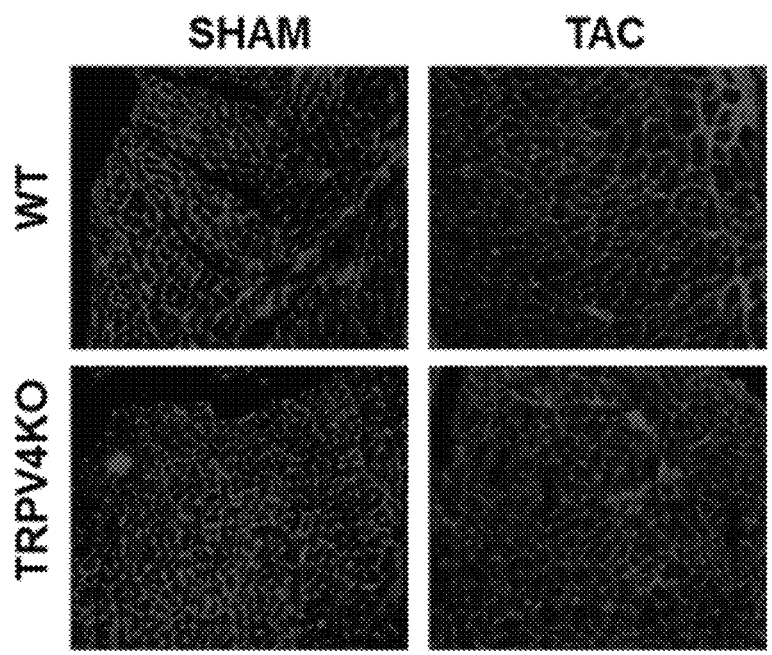
FIG. 3A shows the WGA-staining showing cardiomyocyte cross-sectional area which is increased in WT mice after TAC but not in TRPV4KO mice.

FIG. 3A shows the WGA-staining showing cardiomyocyte cross-sectional area which is increased in WT mice after TAC but not in TRPV4KO mice.

Figure 3B:
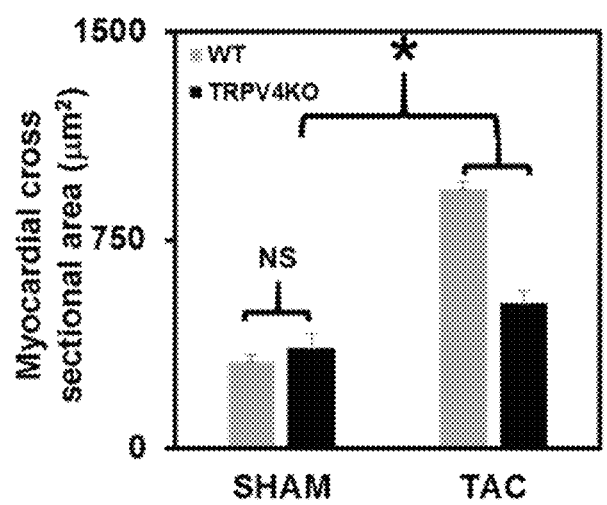
FIG. 3B shows the myocardial cross sectional area (μm²) for WT and TRPV4KO for SHAM and TAC (transverse aortic constriction).

FIG. 3B shows the myocardial cross sectional area ($\mu m^2$) for WT and TRPV4KO for SHAM and TAC (transverse aortic constriction).

Figure 3C:
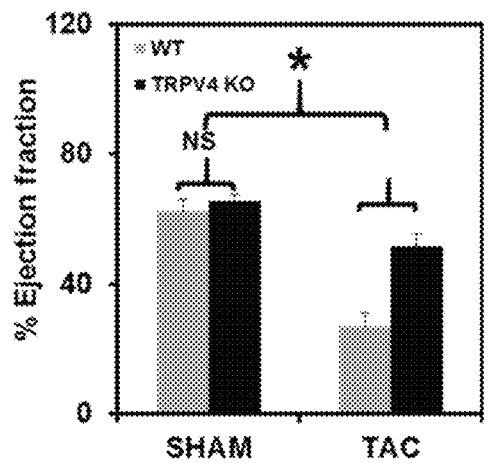
FIG. 3C shows the % ejection fraction for WT and TRPV4KO for SHAM and TAC.

The echocardiographic analysis shows cardiac function (ejection fraction and fractional shortening) is preserved in TRPV4KO mice post-TAC. FIG. 3C shows the % ejection fraction (% EF) for WT and TRPV4KO for SHAM and TAC. FIG. 3D shows collagen staining of WT-TAC and V4KO-TAC hearts, where TRPV4 absence decreased cardiac fibrosis.

Figure 3E:
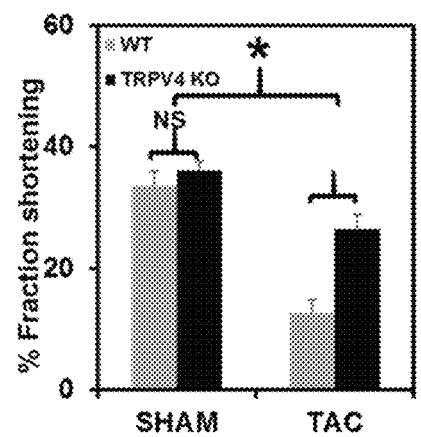
FIG. 3E shows the % fraction shortening for WT and TRPV4KO for SHAM and TAC.
Figure 3D:
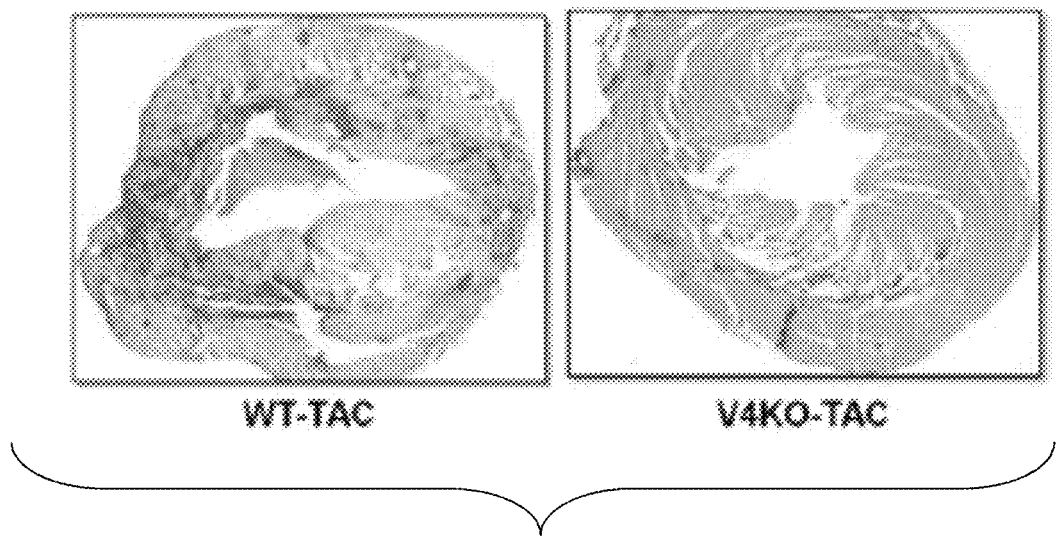
FIG. 3D shows collagen staining of WT-TAC and V4KO-TAC hearts where TRPV4 absence decreased cardiac fibrosis.

FIG. 3E shows the % fractional shortening for WT and TRPV4KO mice for SHAM and TAC.

Figure 3F:
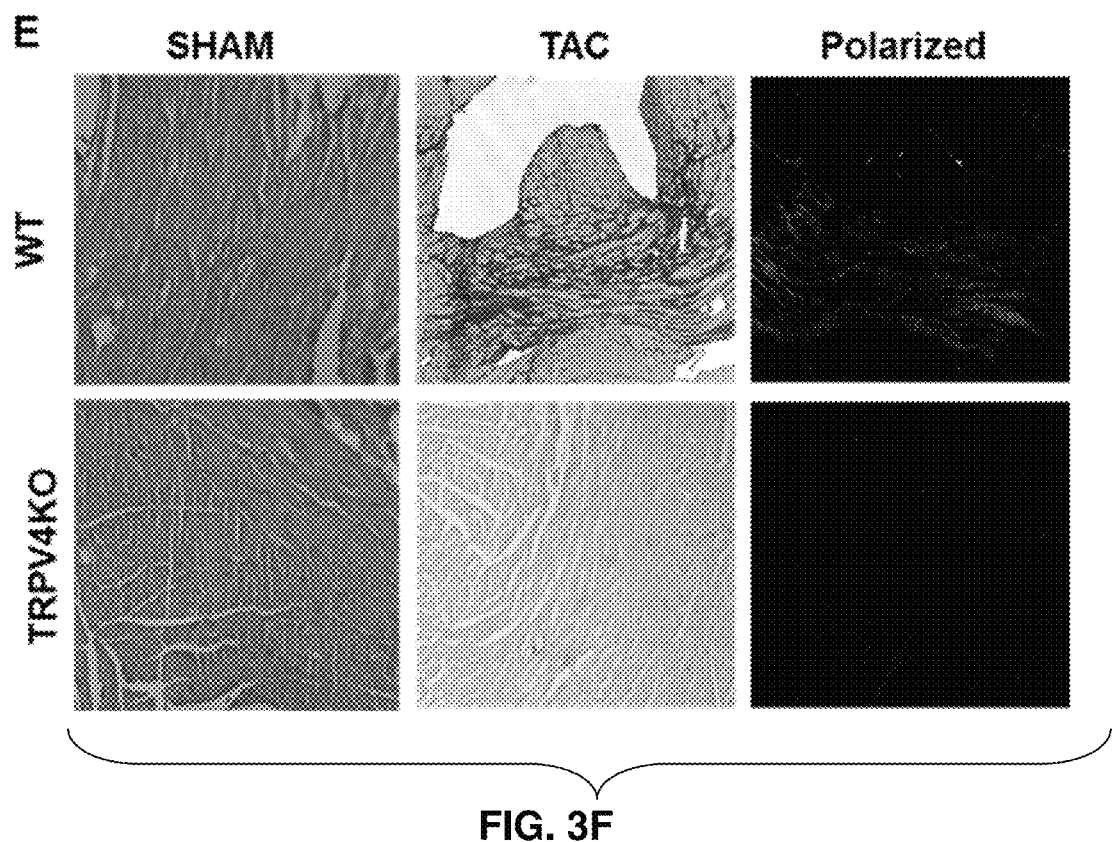
FIG. 3F shows the histological analysis of heart sections showing robust cardiac fibrosis (Picrosirius-red staining) in WT-TAC hearts which is completely absent in TRPV4KO-TAC hearts.

FIG. 3F shows the histological analysis of heart sections showing robust cardiac fibrosis (Picrosirius-red staining) in WT-TAC hearts which is completely absent in TRPV4KO-TAC hearts.

Figure 3G:
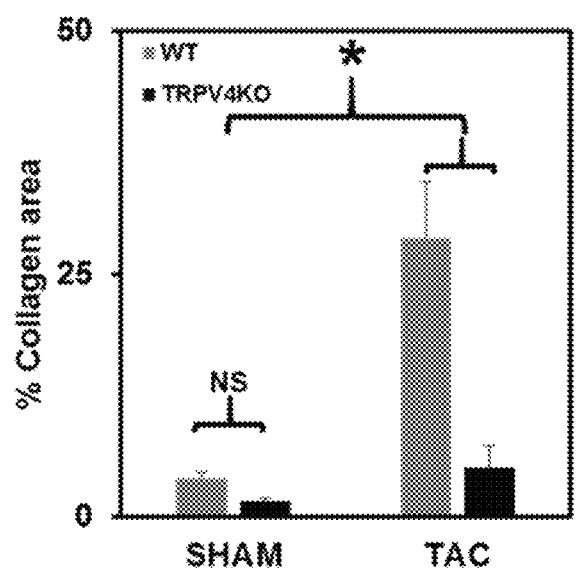
FIG. 3G shows the % collagen area for WT and TRPV4KO for SHAM and TAC.

FIG. 3G shows the % collagen area for WT and TRPV4KO for SHAM and TAC.

Figure 4:
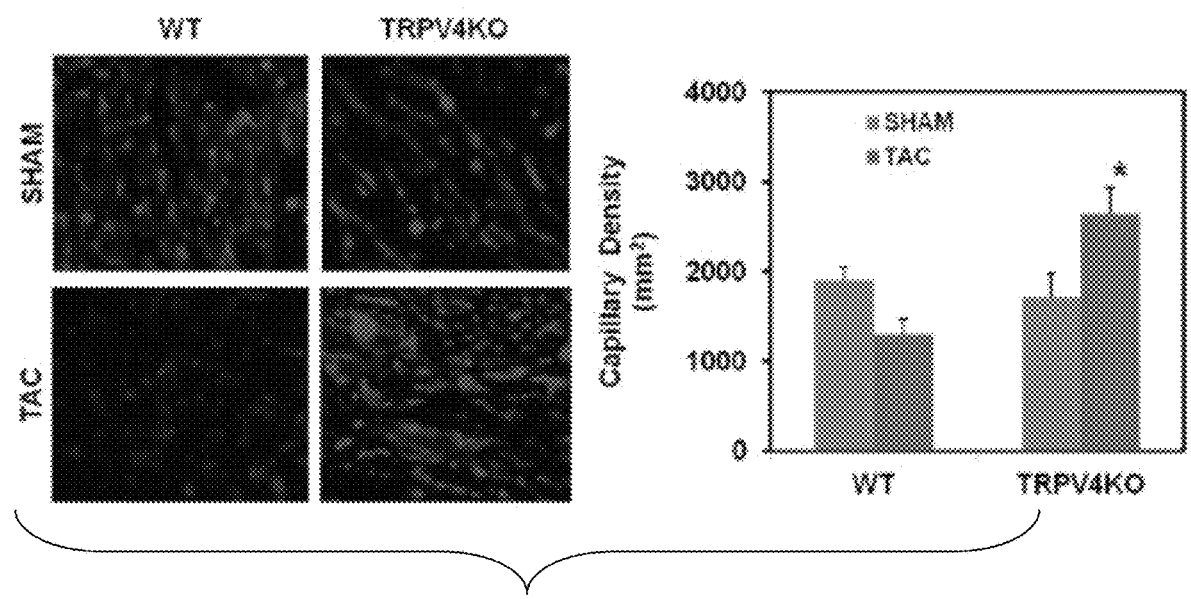
FIG. 4 shows increased coronary angiogenesis post-TAC in TRPV4KO mice, as evidenced by increased capillary density (CD31-red).

Interestingly, exposure to TAC for 28 days significantly increased capillary density (CD31 staining) in TRPV4 KO hearts compared to WT heart (FIG. 4). This indicates increased coronary angiogenesis in TRPV4 KO mice. Taken together, these findings indicate that the absence of TRPV4 channels improves cardiac function and remodeling following pressure-overload. Without wishing to be bound by theory, it is believed that this effect occurs by increasing coronary angiogenesis and decreasing cardiac fibrosis.

Figure 5A:
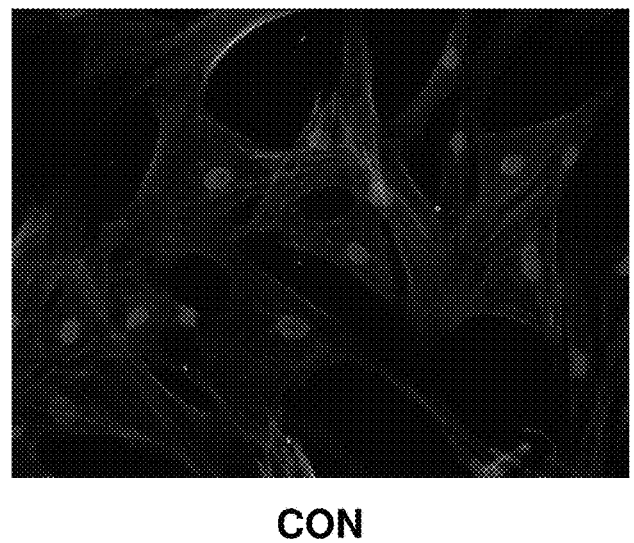
FIGS. 5A-5C show immunofluorescence images showing that the attenuation of TGF-b1-induced differentiation of human ventricular fibroblasts in the presence of TRPV4 inhibitor AB159908 (AB1) (Red: Actin; Green: α-SMA; Blue: DAPI)
Figure 5B:
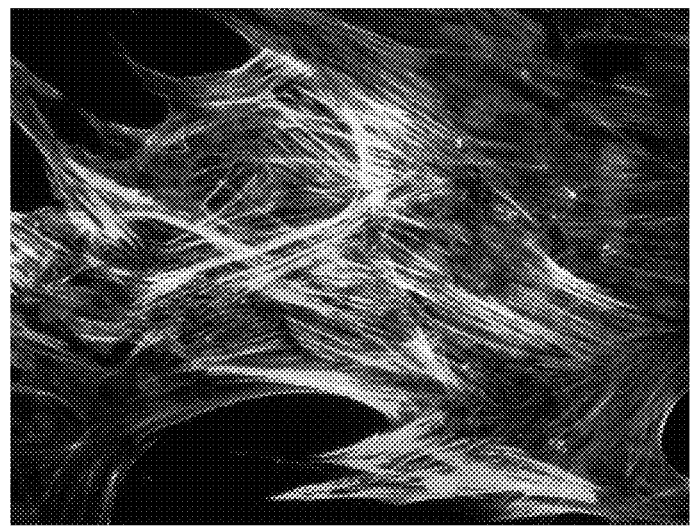
Figure 5C:
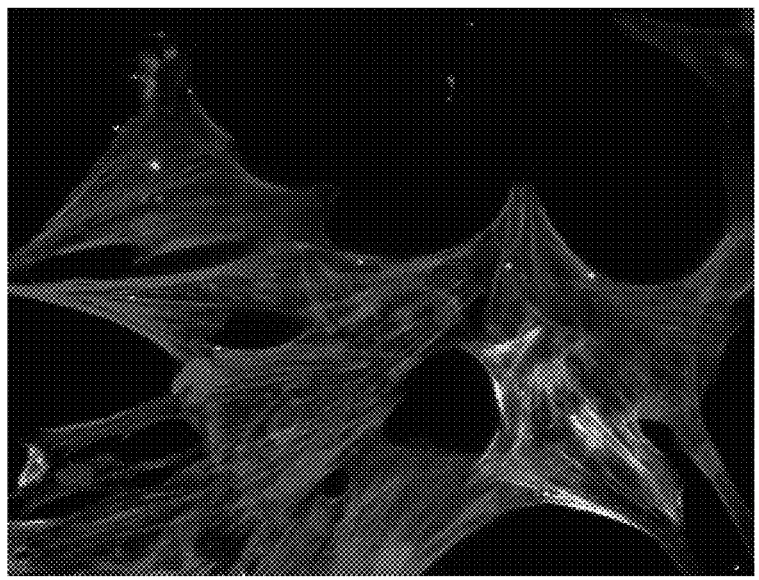

Example 2—TRPV4 Channels are Required for Human Cardiac Fibroblast Differentiation to Myofibroblasts Immunofluorescence images showing that the attenuation of TGF-b1-induced differentiation of human ventricular fibroblasts in the presence of TRPV4 inhibitor AB159908 (AB1) (Red: Actin; Green: α-SMA; Blue: DAPI) FIG. 5A shows the control; FIG. 5B shows TGFβ1; and, FIG. 5C shows AB1+TGFβ1.

Example 3—Absence of TRPV4 Preserves Cardiac Function Following Myocardial Infarction (MI)

To evaluate the physiological significance of the in vitro findings, myocardial infarction was induced in TRPV4 KO mice by LAD ligation. Wild type and sham mice were used as controls. Cardiac function was assessed using 2D and PW Doppler echocardiography on mice 8 weeks following MI. Fibrosis was measured in hearts isolated 8 weeks post-MI from WT and TRPV4 KO mice by staining with picrosirius red and visualized with bright-field and polarized microscopy.

Figure 6A:
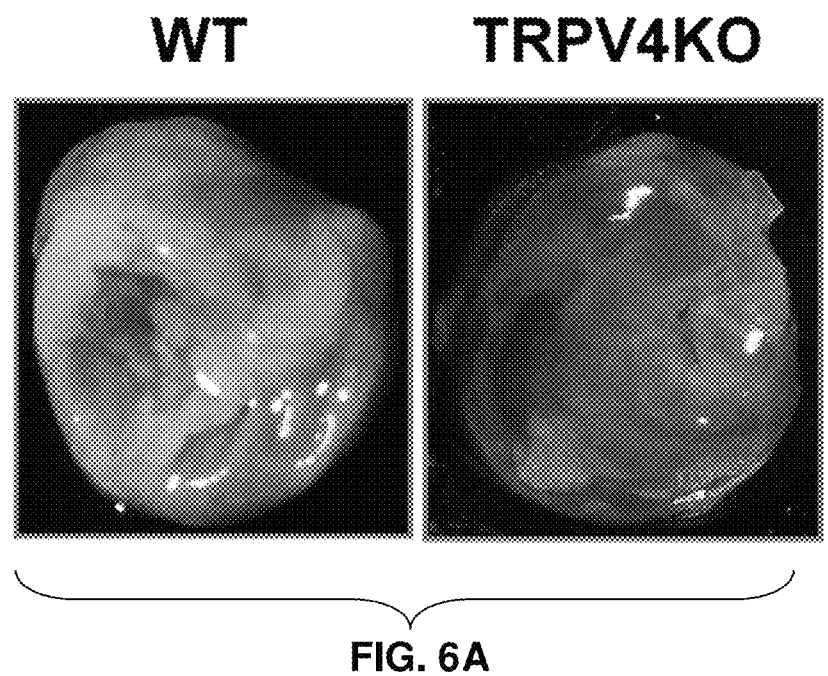
FIG. 6A are photographs showing images of the WT and TRPV4 KO mouse hearts after MI surgery.

FIG. 6A are photographs showing hearts from WT and TRPV4KO mice were subjected to myocardial infarction (MI) surgeries by ligating LAD and followed for 8 weeks.

Figure 6B:
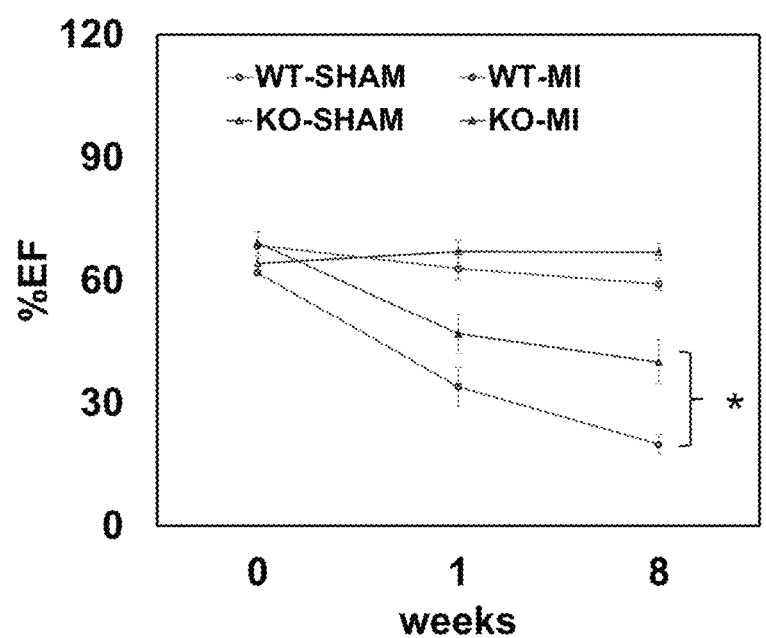
FIG. 6B shows the % EF (ejection fraction=EF) for WT-SHAM, KO-SHAM, WT-MI and KO-MI mice.
Figure 6C:
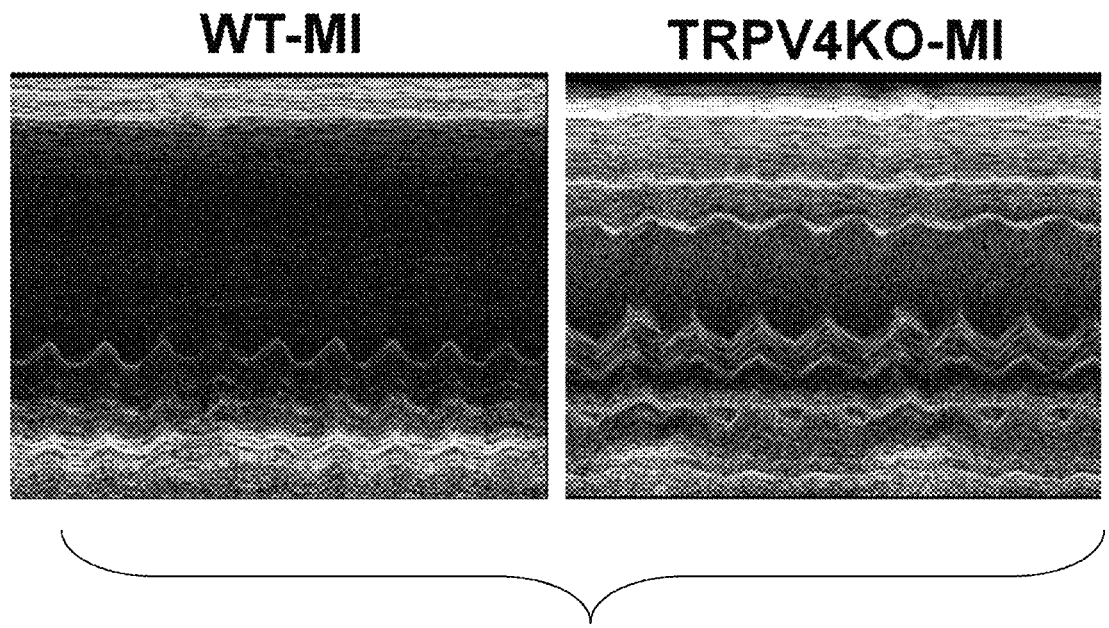
FIG. 6C shows representative M-mode echocardiography images of hearts from WT and TRPV4KO mice, post-MI.
Figure 6D:
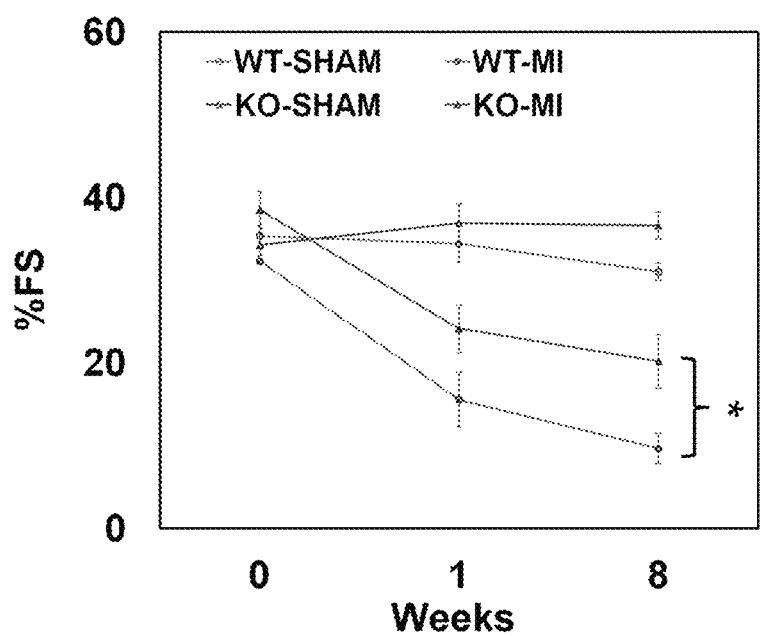
FIG. 6D shows the % FS (fractional fraction) for WT-SHAM, KO-Sham, WT-MI and KO-MI mice.

FIG. 6B shows the % EF (ejection fraction=EF) for WT-SHAM, KO-SHAM, WT-MI and KO-MI. FIG. 6C shows representative M-mode echocardiography images of hearts. FIG. 6D shows the % FS (fractional shortening) for WT-SHAM, KO-Sham, WT-MI and KO-MI.

Echocardiographic analysis showing cardiac function (ejection fraction (EF) shown in FIG. 6B; fractional shortening (FS) shown in FIG. 6D) is preserved in TRPV4KO mice post-MI. Note that there is no change in cardiac function in sham hearts from WT and TRPV4KO mice.

Example 4—TRPV4KO Hearts Exhibit Reduced Hypertrophy Following MI

Figure 7A:
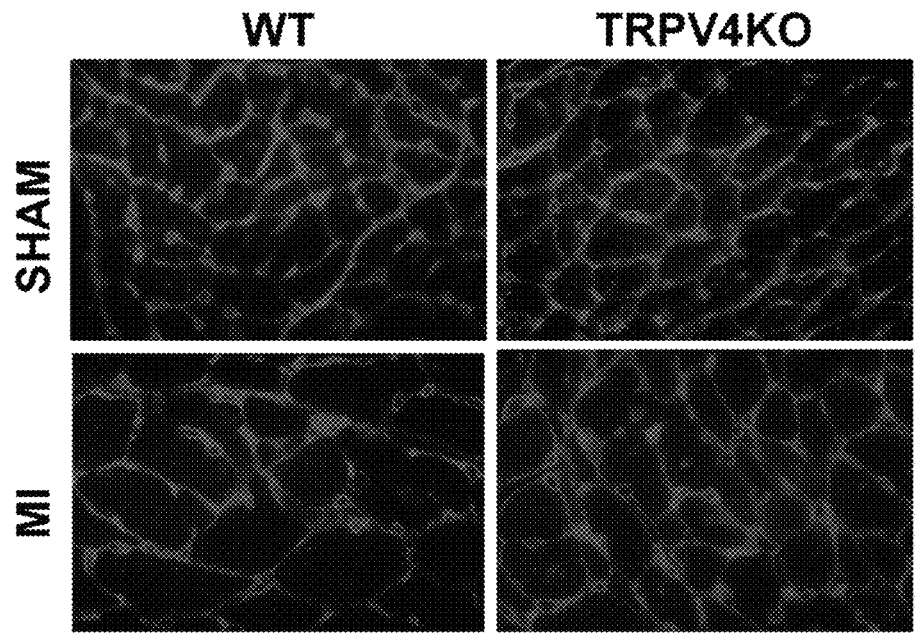
FIG. 7A shows WGA-staining showing cardiomyocyte cross-sectional area which is increased in WT mice after MI but not in TRPV4KO mice.

FIG. 7A shows WGA-staining showing cardiomyocyte cross-sectional area which is increased in WT mice after MI but not in TRPV4KO mice.

Figure 7B:
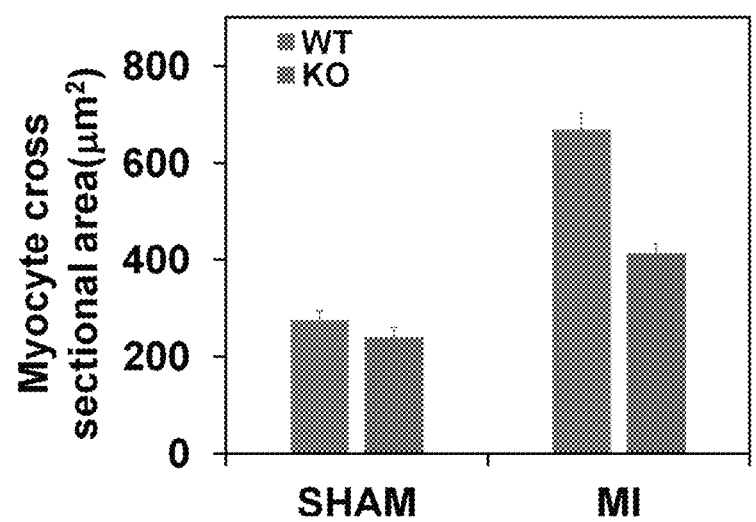
FIG. 7B shows quantification of myocyte cross sectional area ($\mu m^2$) for WT and KO for SHAM and MI (myocardial infarction).

FIG. 7B shows myocyte cross sectional area ($\mu m^2$) for WT and KO for SHAM and MI (myocardial infarction).

Example 5—Cardiomyocyte Apoptosis (Death) is Reduced in TRPV4KO Hearts Post-MI

Figure 8A:
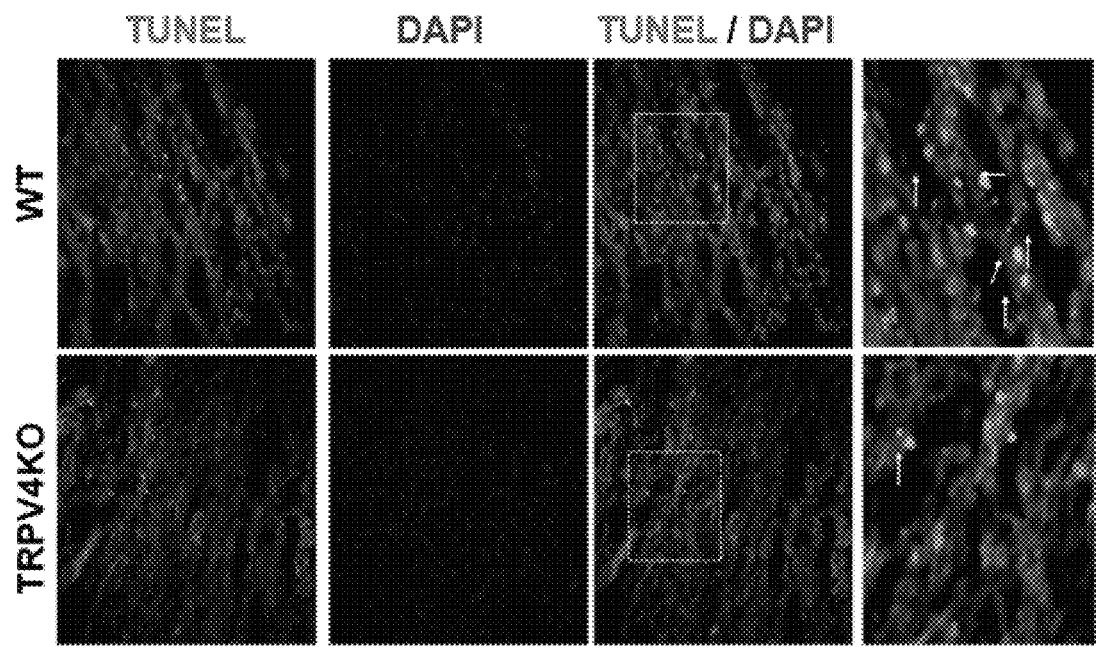
FIG. 8A shows TUNEL-staining showing increased cardiomyocyte apoptosis in WT mice after MI but not in TRPV4KO mice.

FIG. 8A shows TUNEL-staining with increased cardiomyocyte apoptosis in WT mice after MI but not in TRPV4KO mice.

Figure 8B:
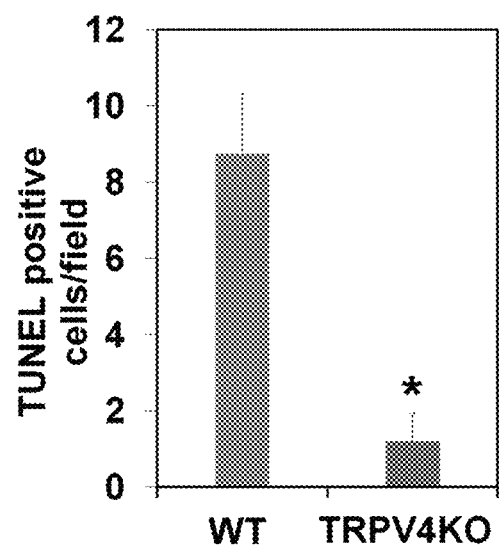
FIG. 8B shows quantification of TUNEL positive cells/field for WT and TRPV4KO.

FIG. 8B shows quantification of TUNEL positive cells/field for WT and TRPV4KO.

Example 6—TRPV4KO Hearts Show Increased Angiogenesis Post-MI

Figure 9A:
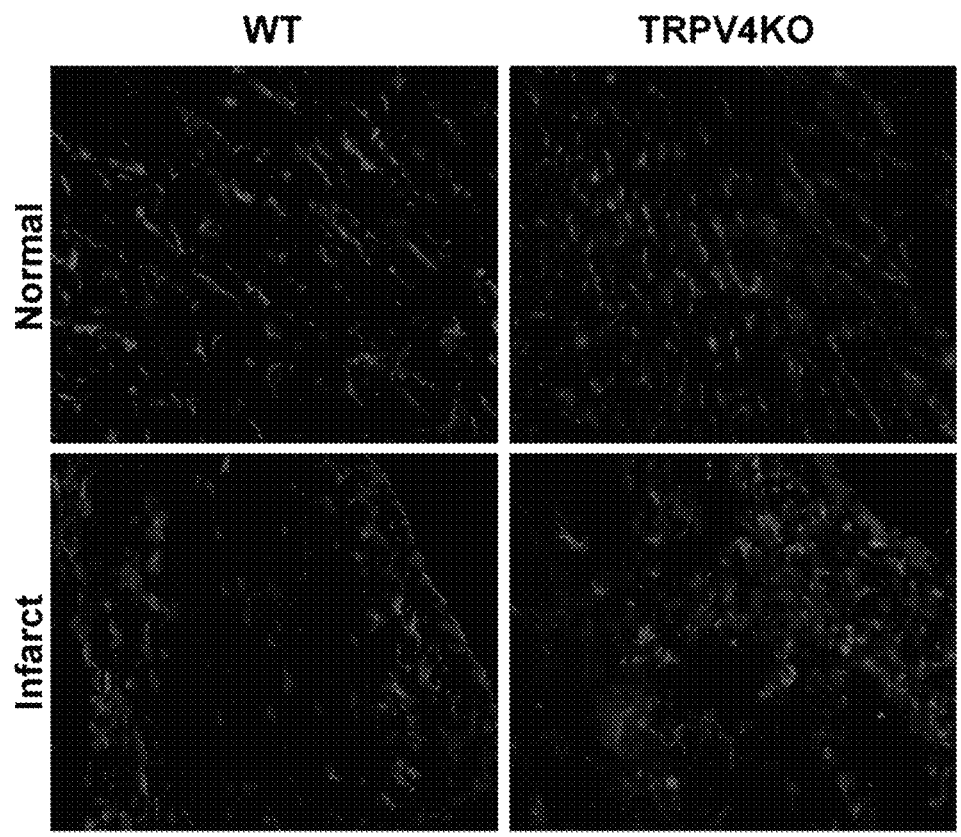
FIG. 9A shows immunofluorescence images showing increased coronary angiogenesis (vascular density; red=CD31; blue: DAPI) in TRPV4 mice after MI compared to WT mice.

FIG. 9A shows immunofluorescence images of increased coronary angiogenesis (vascular density; red=CD31; blue: DAPI) in TRPV4 mice post-MI compared to WT mice.

Figure 9B:
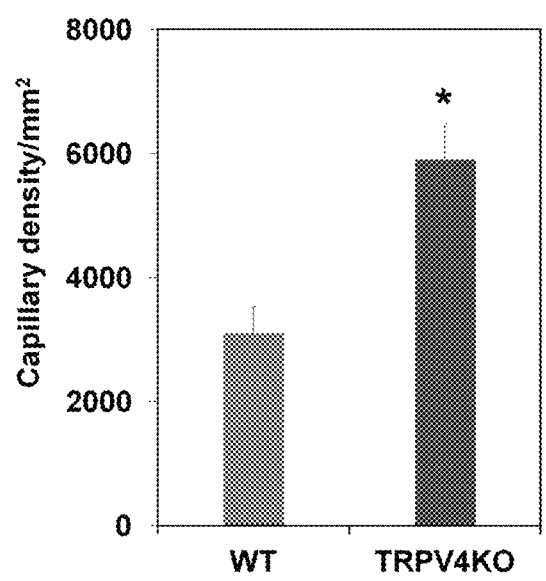
FIG. 9B shows quantification of capillary density/mm² for WT and TRPV4KO.

FIG. 9B shows quantification of capillary density/$mm^2$ for WT and TRPV4KO.

Example 7—TRPV4KO Mice Exhibit Reduced Cardiac Fibrosis Following Myocardial Infarction (MI)

WT and TRPV4KO mice were subjected to MI surgeries and followed for 8 weeks. FIG. 10 shows histological analysis of heart sections showing increased cardiac fibrosis (Picrosirius-red staining) at the infarct zone as well as in remote zone of WT-MI hearts which is significantly reduced in TRPV4KO-MI hearts. Note that intact viable cardiac muscle tissue in the infarct region of TRPV4KO-MI hearts compared to WT mice.

Example 8—an Oral Inhibitor of TRPV4 Protects Heart Post-Myocardial Infarction WT mice were subjected to MI by ligating LAD. MI mice were then given orally a specific TRPV4 antagonist, GSK2193874 (GSK2) (10 mg/Kg/day) or vehicle (0.01% DMSO/water). Echocardiographic analysis revealed that cardiac function (ejection fraction and fractional shortening) is preserved in post-MI mice that are treated with GSK2193874 but not vehicle alone.

FIG. 11A shows % EF (ejection fraction=EF). FIG. 11B shows % FS (fractional shortening=FS).

Example 9—TRPV4 Channel Deletion or Pharmacological Inhibition Protects Heart Against Adverse Remodeling Postmyocardial Infarction WT and TRPV4KO mice were subjected to MI (permanent LAD ligation). 2D-echocardiography revealed that the cardiac function (ejection fraction and fractional shortening) is preserved post-MI in TRPV4KO mice compared to WT mice. Further, reduced fibrosis at infracted and remote zones in TRPV4KO-MI hearts was found, as compared to WT-MI and sham hearts.

TRPV4KO hearts exhibited decreased cardiomyocyte apoptosis (TUNEL assay) and increased capillary density (CD31 staining) post-MI compared to WT hearts.

Orally active TRPV4 antagonist GSK2193874 was given immediately after MI surgery and followed for 5 weeks. Cardiac function analysis revealed that both ejection fraction and fractional shortening were preserved in GSK2193874-treated WT mice compared to either WT or vehicle treated mice. These data show that targeting TRPV4 protects the heart from myocardial infarction induced damage by preserving cardiac structure and function via reduced myocyte apoptosis, diminished fibrosis and increased revascularization, and identifies TRPV4 as a novel therapeutic target for heart failure.

Example 10—CNF is an Activator of Signaling Molecule Downstream of TRPV4

Figure 12:
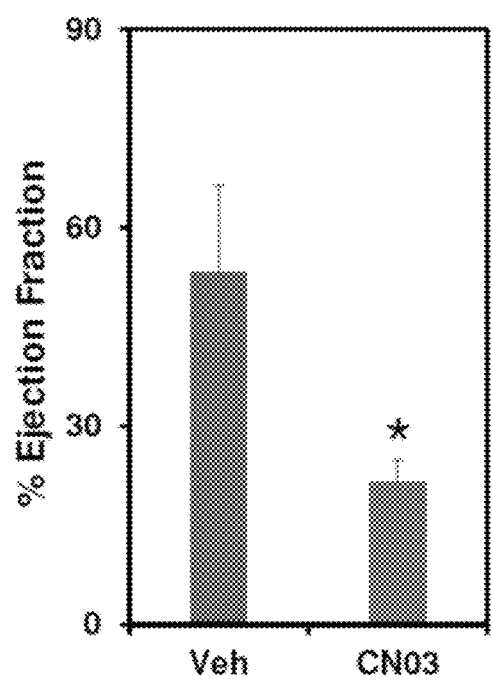
FIG. 12 shows % EF (ejection fraction=EF) of TRPV4KO mice treated with Rho activator CNF-1 (0.1 nM for 4 weeks) or vehicle (0.01% DMSO/water) immediately following myocardial infarction surgeries (MI).

The CNF compound reduces cardiac function in TRPV4 null mice indicating that TRPV4 uses this pathway. FIG. 12 shows % EF (ejection fraction=EF) of TRPV4KO mice treated with Rho activator CNF-1 (0.1 nM for 4 weeks) or vehicle (0.01% DMSO/water) immediately following myocardial infarction surgeries (MI).

Figure 13A:
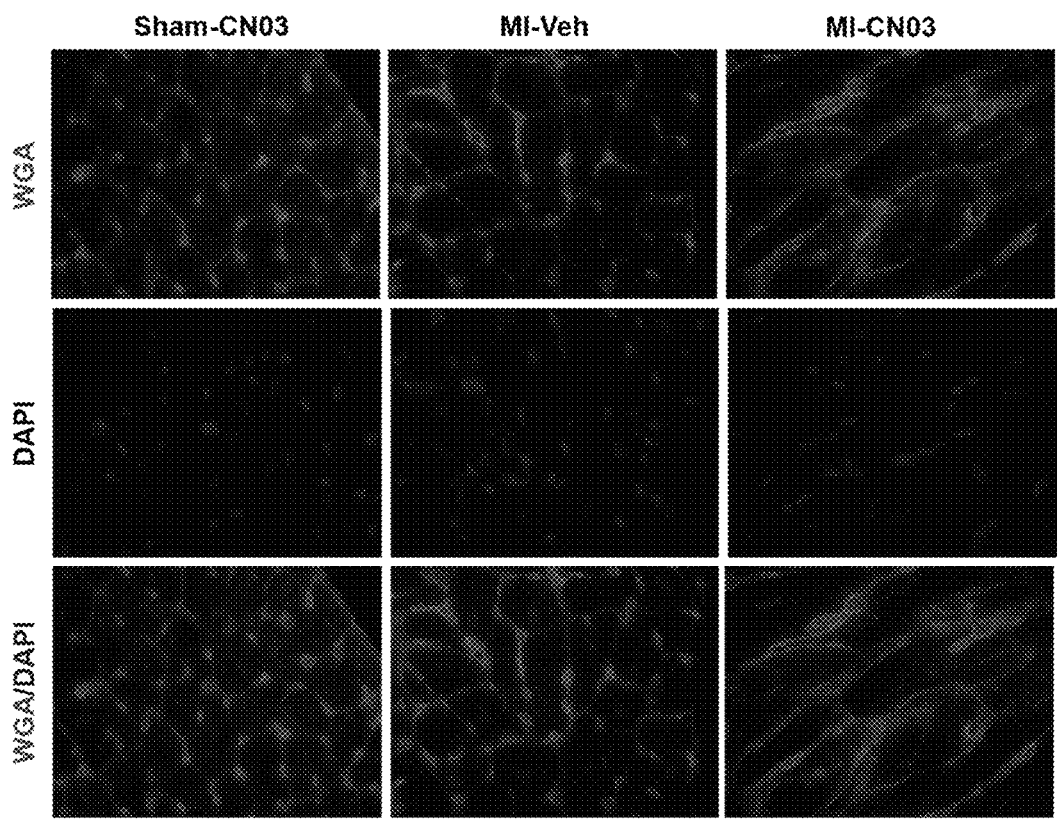
FIG. 13A shows WGA-staining depicting cardiomyocyte cross-sectional area which is increased in TRPV4KO mice treated with CN03 (MI-CN03) but not in vehicle treated (MI-Veh) 4 weeks post-MI.

FIG. 13A shows WGA-staining depicting cardiomyocyte cross-sectional area which is increased in TRPV4KO mice treated with CN03 (MI-CN03) but not in vehicle treated (MI-Veh) 4 weeks post-MI. WGA staining from sham animals served as a control.

Figure 13B:
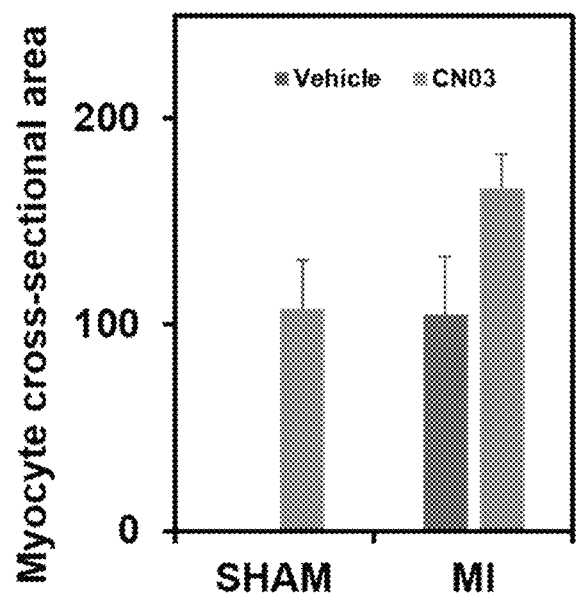
FIG. 13B shows quantification of myocyte cross sectional area ($\mu m^2$) for Sham and MI (myocardial infarction) animals treated with vehicle or CN03.

FIG. 13B shows quantification of myocyte cross sectional area ($\mu m^2$) for Sham and MI (myocardial infarction) animals treated with vehicle or CN03.

Figure 14:
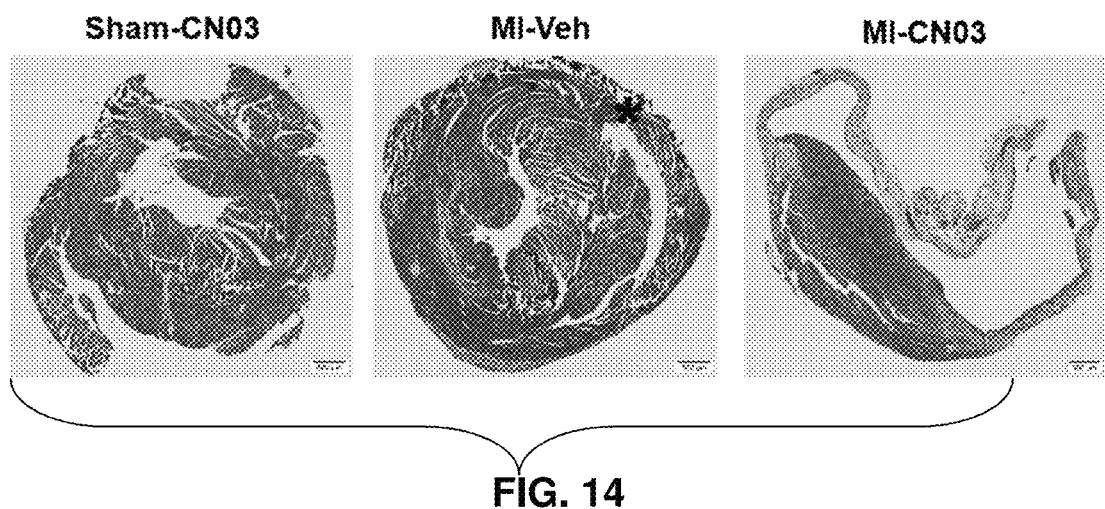
FIG. 14 shows histological analysis of heart sections showing increased cardiac fibrosis (Masson's trichrome staining) at the infarct zone as well as in remote zone of TRPV4KO-MI hearts either treated with vehicle or CN03.

FIG. 14 shows histological analysis of heart sections showing increased cardiac fibrosis (Masson's trichrome staining) at the infarct zone as well as in remote zone of TRPV4KO-MI hearts either treated with vehicle or CN03. Cardiac fibrosis is significantly increased in TRPV4KO-CN03 MI hearts.

Figure 15A:
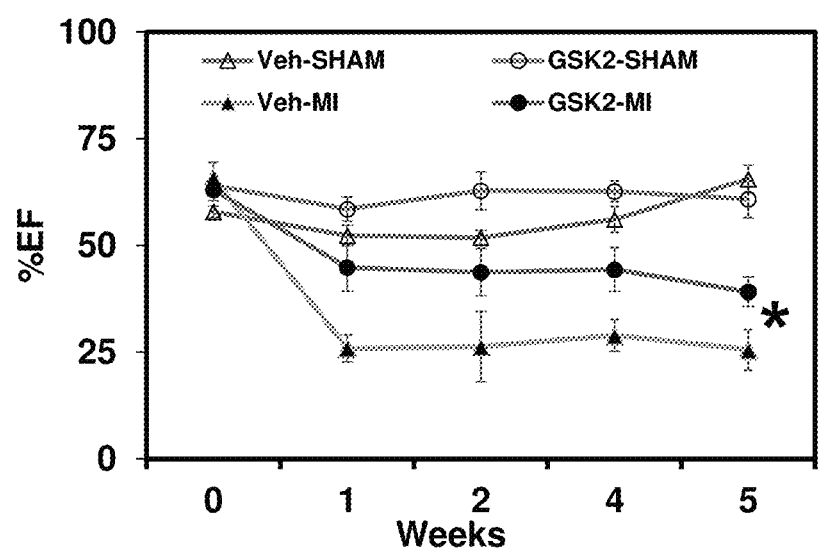
FIG. 15A shows % EF (ejection fraction=EF) for WT mice treated with a specific TRPV4 antagonist, GSK2193874 (GSK2) (10 mg/Kg/day; given orally) or vehicle (0.01% DMSO/water) immediately following myocardial infarction surgeries (MI) or sham up to 5 weeks.
Figure 15B:
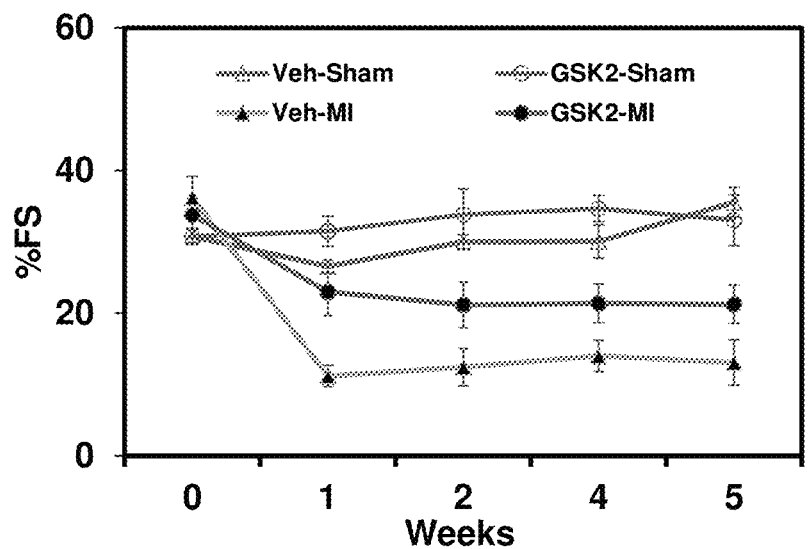
FIG. 15B shows % FS (fractional shortening=FS) for WT mice treated with a specific TRPV4 antagonist, GSK2193874 (GSK2) (10 mg/Kg/day; given orally) or vehicle (0.01% DMSO/water) immediately following myocardial infarction surgeries (MI) or sham up to 5 weeks.

Example 11—TRPV4 Antagonist Protects Heart from Adverse Remodeling after Heart Attack (MI) and Preserves Cardiac Function FIG. 15A shows % EF (ejection fraction=EF) for WT mice treated with a specific TRPV4 antagonist, GSK2193874 (GSK2) (10 mg/Kg/day; given orally) or vehicle (0.01% DMSO/water) immediately following myocardial infarction surgeries (MI) or sham up to 5 weeks. FIG. 15B shows % FS (fractional shortening=FS) for WT mice treated with a specific TRPV4 antagonist, GSK2193874 (GSK2) (10 mg/Kg/day; given orally) or vehicle (0.01% DMSO/water) immediately following myocardial infarction surgeries (MI) or sham up to 5 weeks.

Figure 16:
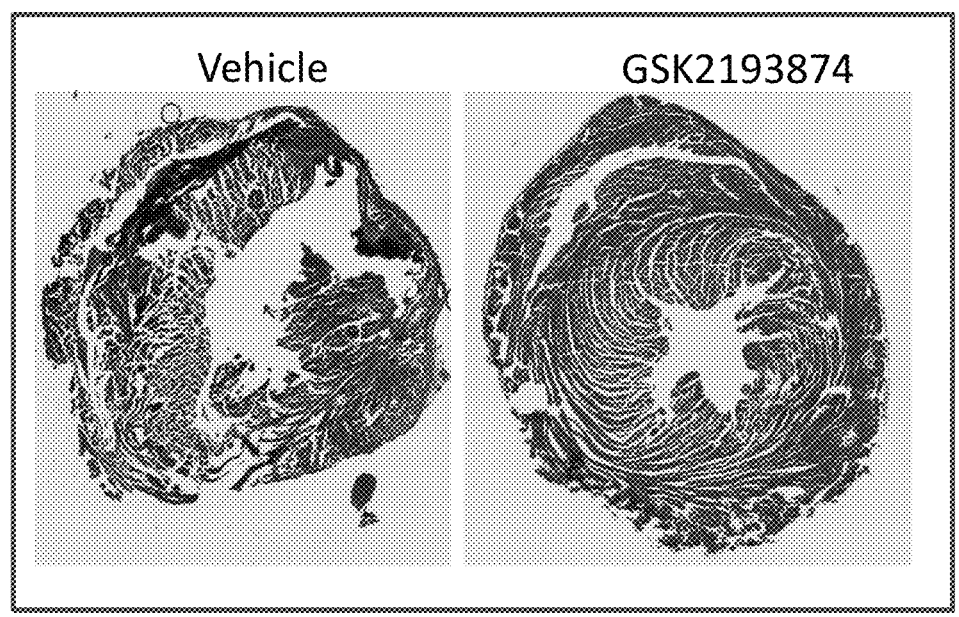
FIG. 16 shows histological analysis of heart sections showing increased cardiac fibrosis (Masson's trichrome staining) at the infarct zone as well as in remote zone of Vehicle treated-MI hearts which is significantly reduced in GSK2 treated-MI hearts.

Example 12—TRPV4 Antagonist Protects Heart from Adverse Remodeling (Cardiac Fibrosis) after Heart Attack (MI) and Preserves Cardiac Function FIG. 16 shows histological analysis of heart sections showing increased cardiac fibrosis (Masson's trichrome staining) at the infarct zone as well as in remote zone of Vehicle treated-MI hearts which is significantly reduced in GSK2 treated-MI hearts.

Figure 17A:
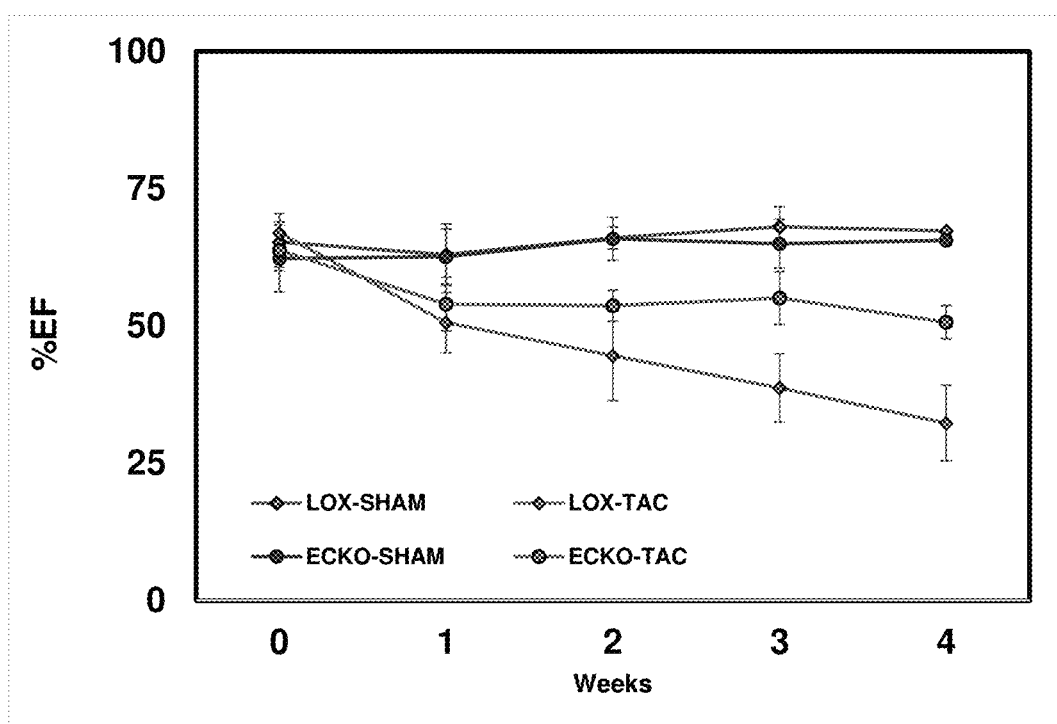
FIG. 17A shows % EF (ejection fraction=EF) of TRPV4fl$^{/fl}$ (floxed) and TRPV4$^{ECKO}$ (endothelial specific knockout of TRPV4) 4 weeks post-TAC.
Figure 17B:
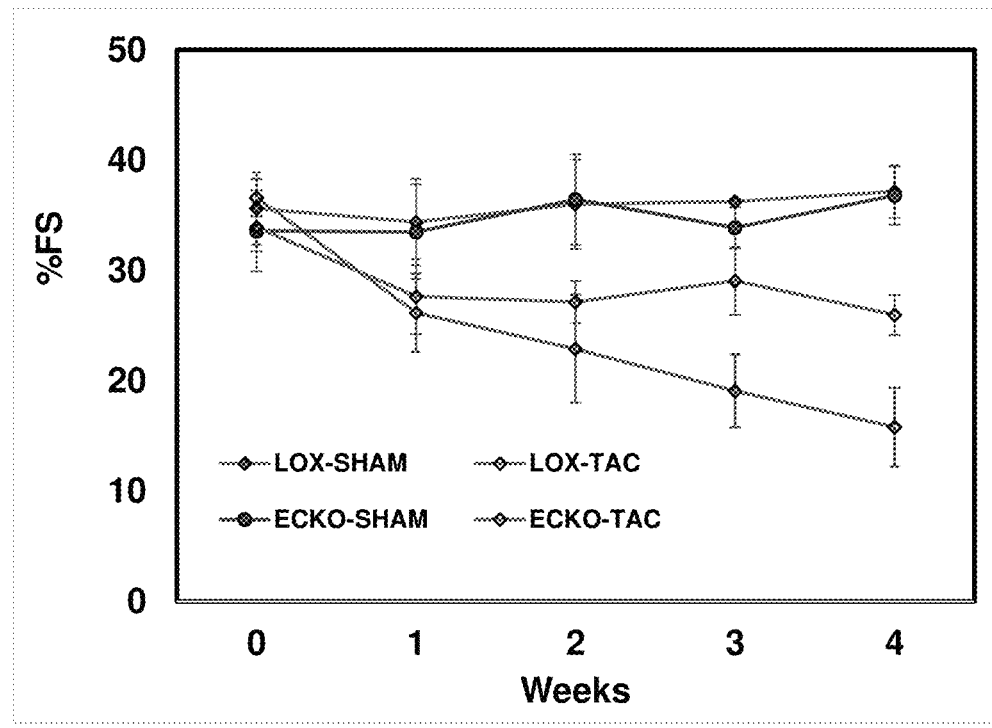
FIG. 17B shows % FS (fractional shortening=FS) of TRPV4fl$^{/fl}$ (floxed) and TRPV4$^{ECKO}$ (endothelial specific knockout of TRPV4) 4 weeks post-TAC.

Deletion of TRPV4 in specific cells (endothelial) protects heart from adverse remodeling after hypertension (TAC) and preserves cardiac function. FIG. 17A shows % EF (ejection fraction=EF) of TRPV4fl$^{fl/fl}$ (floxed) and TRPV4$^{ECKO}$ (endothelial specific knockout of TRPV4) 4 weeks post-TAC. Sham animals served as control. FIG. 17B shows % FS (fractional shortening=FS) of TRPV4fl$^{fl/fl}$(floxed) and TRPV4$^{ECKO}$ (endothelial specific knockout of TRPV4) 4 weeks post-TAC. Sham animals served as control.

Figure 18:
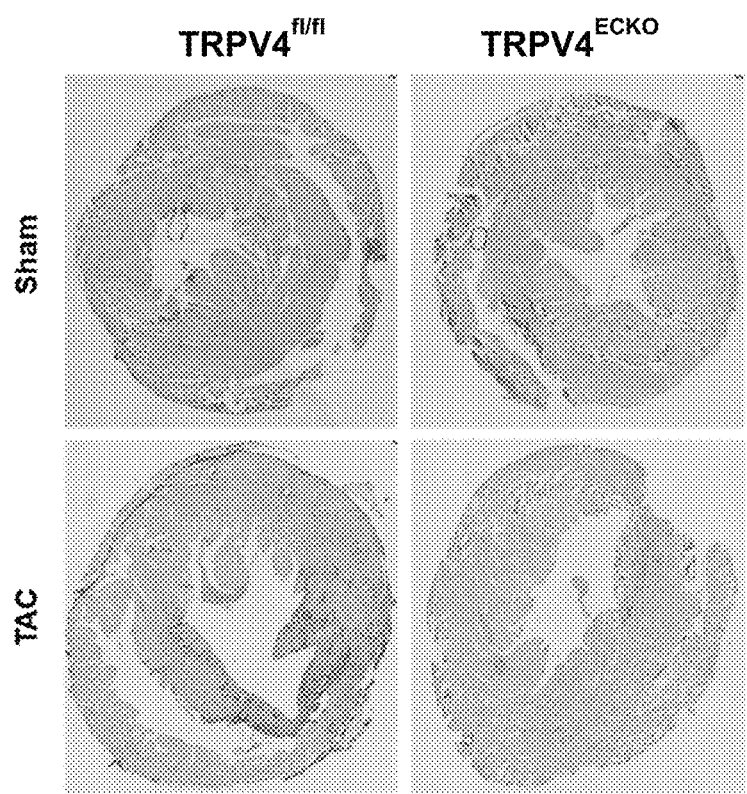
FIG. 18 shows histological analysis of heart sections showing increased cardiac fibrosis (Picrosirius red staining) in TRPV4$^{fl/fl}$ mice which is significantly reduced in TRPV4$^{ECKO}$, post-TAC.

Deletion of TRPV4 in specific cells (endothelial) protects heart from adverse remodeling after hypertension (TAC) and inhibits cardiac fibrosis. FIG. 18 shows histological analysis of heart sections showing increased cardiac fibrosis (Picrosirius red staining) in TRPV4$^{fl/fl}$ mice which is significantly reduced in TRPV4$^{ECKO}$, post-TAC.

Figure 19:
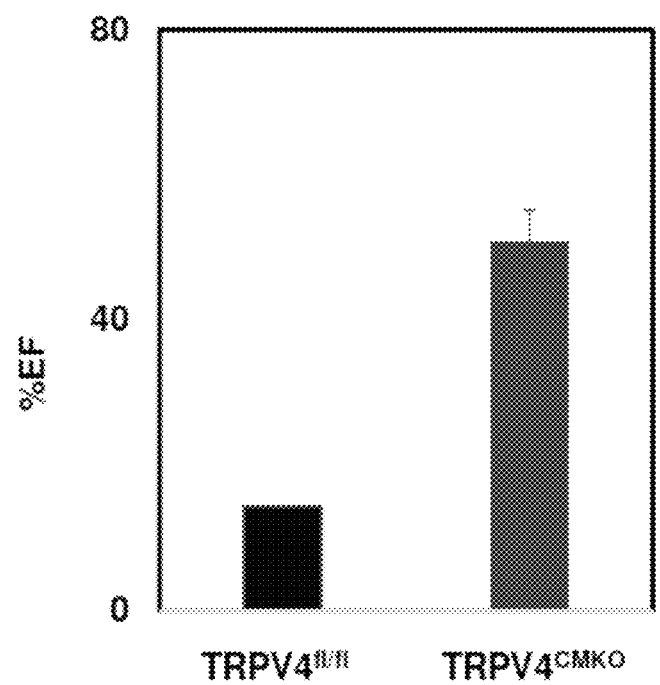
FIG. 19 shows % EF (ejection fraction=EF) of TRPV4fl$^{/fl}$ (floxed) and TRPV4$^{CMKO}$ (cardiomyocyte specific knockout of TRPV4) 4 weeks post-MI.

Deletion of TRPV4 in specific cells (cardiomyocyte) protects heart after heart attack (MI) and preserves cardiac function. FIG. 19 shows % EF (ejection fraction=EF) of TRPV4fl$^{fl/fl}$ (floxed) and TRPV4$^{CMKO}$ (cardiomyocyte specific knockout of TRPV4) 4 weeks post-MI.

Figure 20A:
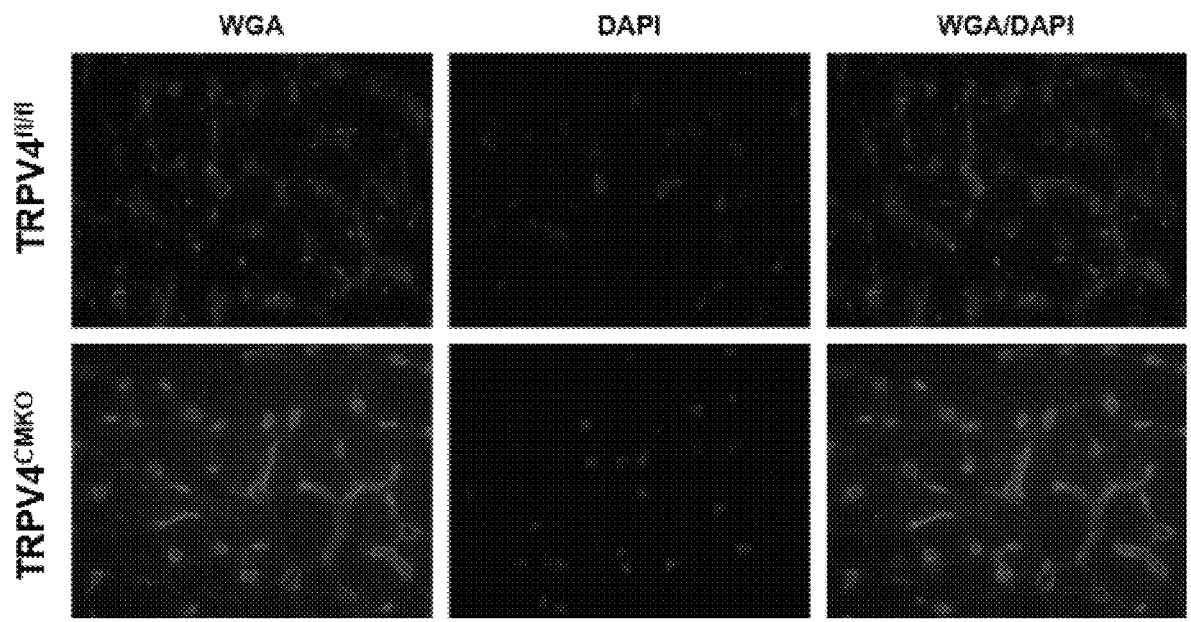
FIG. 20A shows WGA-staining showing cardiomyocyte cross-sectional area which is decreased in TRPV4$^{CMKO}$ mice post-MI compared to TRPV4$^{fl/fl}$ mice.
Figure 20B:
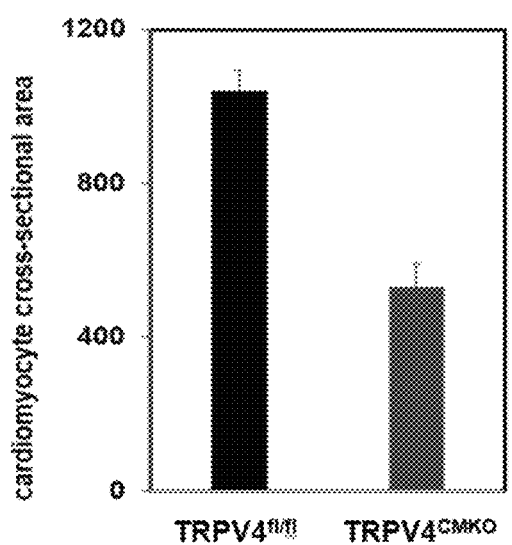
FIG. 20B shows quantification of myocyte cross sectional area ($\mu m^2$) from FIG. 26A.

FIG. 20A shows WGA-staining showing cardiomyocyte cross-sectional area which is decreased in TRPV4$^{CMKO}$ mice post-MI compared to TRPV4$^{fl/fl}$ mice. FIG. 20B shows quantification of myocyte cross sectional area ($\mu m^2$) from FIG. 20A.

Figure 21:
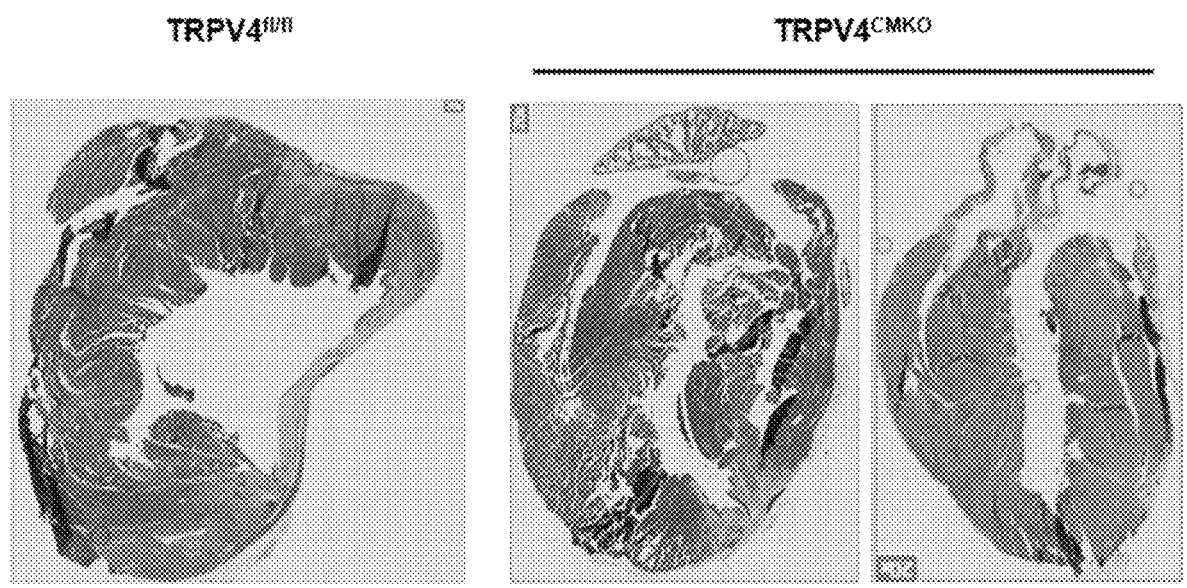
FIG. 21 shows histological analysis of heart sections showing decreased cardiac fibrosis (Masson's trichrome staining) in TRPV4$^{CMKO}$ mice which is significantly increased in TRPV4$^{fl/fl}$, post-MI.

FIG. 21 shows histological analysis of heart sections showing decreased cardiac fibrosis (Masson's trichrome staining) in TRPV4$^{CMKO}$ mice which is significantly increased in TRPV4$^{fl/fl}$, post-MI.

Formulations and Dosages

The TRPV4 inhibitor is typically administered at a concentration ranging from about 0.01 µM to about 100 µM, or from about 1 µM to about 75 µM, or from about 5 µM to about 50 µM. In certain non-limiting examples, the TRPV4 inhibitor is administered at a concentration of about 10 µM.

The TRPV4 inhibitor can be formulated into a pharmaceutical composition. Pharmaceutical compositions of the present disclosure comprise an effective amount of a TRPV4 inhibitor, and/or additional agents, dissolved or dispersed in a pharmaceutically acceptable carrier, diluents, or excipient. The phrases "pharmaceutically acceptable" or "pharmacologically acceptable" refer to molecular entities and compositions that produce no adverse, allergic, or other untoward reaction when administered to an animal, such as, for example, a human. The preparation of a pharmaceutical composition that contains a TRPV4 inhibitor and at least one additional active ingredient will be known to those of skill in the art in light of the present disclosure, as exemplified by Remington's Pharmaceutical Sciences, 2018, incorporated herein by reference. Moreover, for animal (e.g., human) administration, it is understood that preparations should meet sterility, pyrogenicity, general safety, and purity standards as required by the FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2018, incorporated herein by reference).

The actual dosage amount of a composition disclosed herein administered to an animal or human patient can be determined by physical and physiological factors such as body weight, severity of condition, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound (i.e., a TRPV4 inhibitor). In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions. In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, Remington's Pharmaceutical Sciences, 2018). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Certain embodiments of the methods and compositions disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for in vivo treating a cardiac condition in a human subject, the method comprising:
    administering a therapeutically effective in vivo amount of a TRPV4 inhibitor to a human subject in need thereof, wherein the cardiac condition comprises cardiac fibrosis;
    wherein the TRPV4 inhibitor comprises one or more of:
    2,4-dichloro-N-isopropyl-N-(2-isopropylaminoethyl) benzenesulfonamide (AB159908 or RN1734),
    2-methyl-1-[3-(4-morpholinyl)propyl]-5-phenyl-N-[3-(trifluoromethyl)phenyl]-1H-pyrrole-3-carboxamide (HC-067047),
    N-[2-(4-chlorophenyl)ethyl]-1,3,4,5-tetrahydro-7,8-dihydroxy-2H-2-benzazepine-2-carbothioamide (capsazepine),
    3,7-dimethyl-2,6-octadienal (citral),
    N-(4-(2-(benzyl(methyl)amino)ethyl)phenyl)-5-(pyridin-3-yl)thiazol-2-amine (GSK205), and
    3-([1,4'-bipiperidin]-1'-ylmethyl)-7-bromo-N-(1-phenyl-cyclopropyl)-2-[3-(trifluoromethyl)phenyl]-4-quinolinecarboxamide (GSK2193874);
    inhibiting TRPV4 activity/function and expression in cardiac tissue in the human subject; and,
    reducing the rate of formation of fibrotic tissue in the heart of the subject.

2. The method of claim 1, wherein the cardiac condition comprises cardiac fibrosis not caused by myocardial infarction.

3. The method of claim 1, wherein the TRPV4 inhibitor comprises 3-([1,4'-bipiperidin]-1'-ylmethyl)-7-bromo-N-(1-phenylcyclopropyl)-2-[3-(trifluoromethyl)phenyl]-4-quinolinecarboxamide (GSK2193874).

4. The method of claim 1, wherein the TRPV4 inhibitor is formulated in a composition with one or more pharmaceutically acceptable excipients, diluents, or carriers.

5. The method of claim 1, wherein the TRPV4 inhibitor is administered at a concentration ranging from about 0.01 µM to about 100 µM.

6. The method of claim 1, wherein the TRPV4 inhibitor is administered at a concentration of about 10 µM.

7. The method of claim 1, wherein the TRPV4 inhibitor is co-administered with an ischemic heart disease treatment selected from the group consisting of: organic nitrates, beta blockers, calcium channel blockers, statins, antiplatelets, ACE inhibitors, and combinations thereof.

8. The method of claim 1, wherein the TRPV4 inhibitor is administered via an oral solid dosage form.

9. The method of claim 1, wherein the TRPV4 inhibitor is administered parenterally.

* * * * *